(12) United States Patent
Peterson et al.

(10) Patent No.: US 7,407,500 B2
(45) Date of Patent: **\*Aug. 5, 2008**

(54) OSMOTIC DELIVERY SYSTEM FLOW MODULATOR APPARATUS AND METHOD

(75) Inventors: Lewis L. Peterson, Woodside, CA (US); Fred H. Maruyama, San Jose, CA (US); Houdin Dehnad, El Granada, CA (US); Lawton Hom, San Francisco, CA (US); Kevin S. Ly, San Jose, CA (US); Craig R. Davis, Newark, CA (US); John R. Peery, Stanford, CA (US)

(73) Assignee: ALZA Corporation, Mountain View, CA (US)

( * ) Notice: Subject to any disclaimer, the term of this patent is extended or adjusted under 35 U.S.C. 154(b) by 274 days.

This patent is subject to a terminal disclaimer.

(21) Appl. No.: 10/994,615

(22) Filed: Nov. 22, 2004

(65) Prior Publication Data

US 2005/0131389 A1 Jun. 16, 2005

Related U.S. Application Data

(62) Division of application No. 10/279,957, filed on Oct. 25, 2002, now Pat. No. 6,840,931, which is a division of application No. 09/122,073, filed on Jul. 24, 1998, now Pat. No. 6,524,305.

(60) Provisional application No. 60/053,690, filed on Jul. 25, 1997.

(51) Int. Cl.
*A61K 9/22* (2006.01)
*A61F 13/00* (2006.01)

(52) U.S. Cl. .................. 604/892.1; 604/890.1; 424/422

(58) Field of Classification Search .............. 604/890.1, 604/892.1, 288.01–288.04; 424/422
See application file for complete search history.

(56) References Cited

U.S. PATENT DOCUMENTS 3,732,865 A 5/1973 Higuchi et al.

(Continued)

FOREIGN PATENT DOCUMENTS

WO WO91/07160 5/1991

(Continued)

OTHER PUBLICATIONS

International Search Report of International Searching Authority, Re:PCT/US98/14813 Date of Mailing of Search Report: Feb. 5, 1999.

*Primary Examiner*—Kevin C. Sirmons
*Assistant Examiner*—Benjamin Huh
(74) *Attorney, Agent, or Firm*—Angela N. Nwaneri

(57) ABSTRACT

An osmotic delivery system flow modulator assembly, an osmotic delivery system with a flow modulator assembly, and a method of assembling an osmotic delivery system. The osmotic delivery system flow modular assembly includes a body having a hole located through the body and communicating two opposing ends of the body. The use of the osmotic delivery system flow modulator assembly lessens the chance that air or gas pockets will form in the enclosure of the osmotic delivery system during assembly of the system. Because less air is within the osmotic delivery system, performance of the system is enhanced. Use of the flow modulator assembly also lessens the chance that beneficial agent will be wasted during assembly of the osmotic delivery system.

8 Claims, 4 Drawing Sheets

U.S. PATENT DOCUMENTS

| | | | |
|---|---|---|---|
| 3,831,813 A | 8/1974 | Latham, Jr. | |
| 3,995,631 A | 12/1976 | Higuchi et al. | |
| 3,995,632 A | 12/1976 | Nakano et al. | |
| 4,111,202 A | 9/1978 | Theeuwes | |
| 4,243,030 A | 1/1981 | Lynch et al. | |
| 4,320,758 A | 3/1982 | Eckenhoff et al. | |
| 4,340,054 A | 7/1982 | Michaels | |
| 4,373,527 A | 2/1983 | Fischell | |
| 4,439,196 A | 3/1984 | Higuchi | |
| 4,552,561 A | 11/1985 | Eckenhoff et al. | |
| 4,639,244 A | 1/1987 | Rizk et al. | |
| 4,747,847 A | 5/1988 | Magruder et al. | |
| 4,865,845 A | 9/1989 | Eckenhoff et al. | |
| 5,106,627 A | 4/1992 | Aebischer et al. | |
| 5,223,265 A | 6/1993 | Wong | |
| 5,279,608 A | 1/1994 | Cherif Cheikh | |
| 5,308,348 A | 5/1994 | Balaban et al. | |
| 5,312,389 A | 5/1994 | Theeuwes et al. | |
| 5,312,390 A | 5/1994 | Wong | |
| 5,431,919 A | 7/1995 | Maruyama et al. | |
| 5,456,679 A * | 10/1995 | Balaban et al. | 604/892.1 |
| 5,474,785 A | 12/1995 | Wright et al. | |
| 5,690,952 A | 11/1997 | Magruder et al. | |
| 5,728,396 A | 3/1998 | Peery et al. | |
| 6,524,305 B1 | 2/2003 | Peterson et al. | |
| 6,840,931 B2 | 1/2005 | Peterson et al. | |

FOREIGN PATENT DOCUMENTS

| | | |
|---|---|---|
| WO | WO94/09743 | 5/1994 |

* cited by examiner

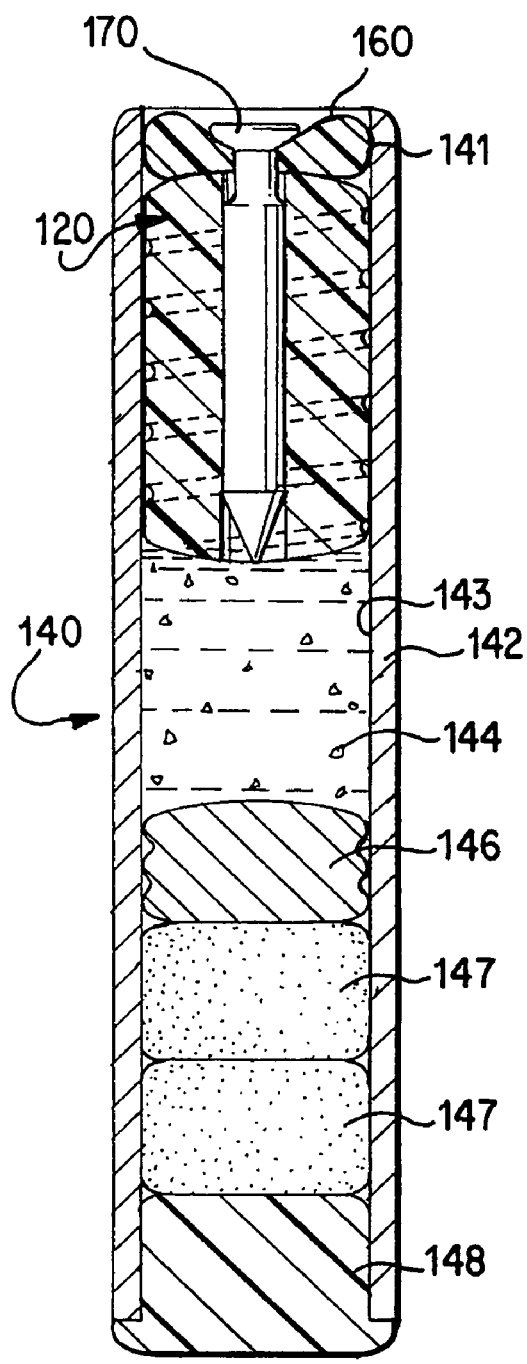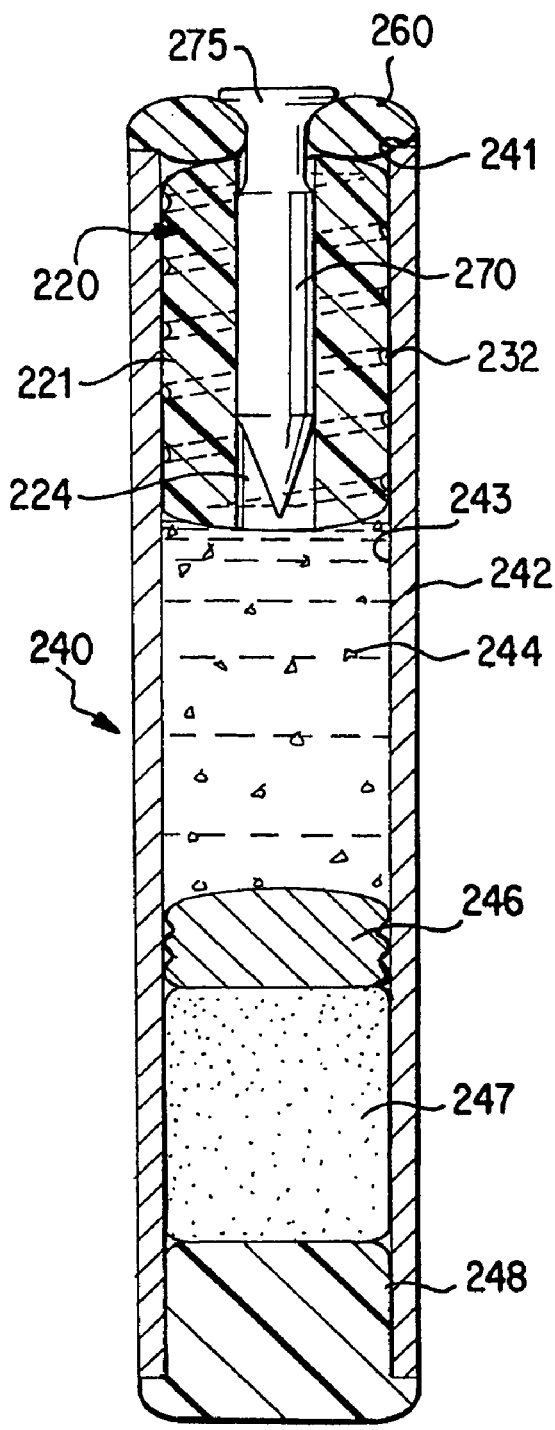

OSMOTIC DELIVERY SYSTEM FLOW MODULATOR APPARATUS AND METHOD

CROSS REFERENCE TO RELATED APPLICATIONS

This application is a divisional of U.S. application Ser. No. 10/279,957, filed Oct. 25, 2002, now U.S. Pat. No. 6,840,931 which is a divisional of U.S. application Ser. No. 09/122,073, filed Jul. 24, 1998 now U.S. Pat. No. 6,524,305, which claims the benefit of U.S. Provisional Application No. 60/053,690 filed Jul. 25, 1997, pursuant to 35 U.S.C. § 119(e), all of which are hereby incorporated by reference.

BACKGROUND OF THE INVENTION

The present invention relates to osmotic delivery systems for delivering beneficial agents, and more particularly, to an osmotic delivery system flow modulator.

Controlled delivery of beneficial agents, such as drugs, in the medical and veterinary fields is accomplished by a variety of methods. One method of controlled prolonged delivery of beneficial agents involves the use of osmotic delivery systems. These devices can be implanted to release beneficial agents in a controlled manner over a pre-selected time or administration period. In general, osmotic delivery systems operate by imbibing fluid from the outside environment and releasing corresponding amounts of the beneficial agent.

Osmotic delivery systems, commonly referred to as "osmotic pumps," generally include some type of a capsule or enclosure having a wall which selectively permits liquid to enter the interior of the enclosure which contains a liquid attracting osmotic agent. The absorption of liquid by the osmotic agent within the enclosure creates osmotic pressure within the enclosure which, in turn, causes the beneficial agent to be delivered from the enclosure. The osmotic agent may be the beneficial agent and/or a formulation containing the same delivered to the patient. However, in many cases, a separate osmotic agent is used specifically for its ability to draw liquid into the enclosure.

When a separate osmotic agent is used, the osmotic agent may be separated from the beneficial agent within the osmotic delivery system enclosure by a dividing member or movable piston. The structure of the osmotic delivery system does not permit the enclosure to expand when the osmotic agent takes in water and swells. As the osmotic agent expands, it causes the beneficial agent to be discharged through an orifice or delivery port in the enclosure at generally the same rate as a liquid, which is typically water, enters the osmotic agent by osmosis. Osmotic delivery systems may be designed to deliver a beneficial agent at a controlled constant rate, a varying rate, or in a pulsatile manner.

In some known osmotic delivery systems, the osmotic agent is typically shaped as an osmotic tablet, and is placed inside the enclosure. A semipermeable membrane plug is then typically placed in an opening in the enclosure through which the tablet was inserted. The semipermeable membrane plug acts as the wall which selectively permits liquid to enter the interior of the enclosure. Known semipermeable membrane plugs are typically a cylindrical member with ribs, and operate in the same manner as a cork. These semipermeable membrane plugs seal the interior of the enclosure from the exterior environment of use, only permitting certain liquid molecules from the environment of use to permeate through the semipermeable membrane plug into the interior of the enclosure. The rate that the liquid permeates through the semipermeable membrane plug controls the rate at which the osmotic agent expands and drives a desired concentration of beneficial agent from the delivery system through the delivery port. Osmotic delivery systems may control the rate of delivery of the beneficial agent by varying the permeability coefficient of the semipermeable membrane plug.

In known osmotic delivery systems, the beneficial agent exits the osmotic delivery system enclosure through a delivery port. Such delivery ports are typically fashioned in a plug-like member which is inserted into an opening of the osmotic delivery system enclosure. The opening of the enclosure into which the delivery plug is inserted is typically opposite the end of the enclosure which holds the semipermeable membrane plug. Thus, in assembling these osmotic delivery systems, the dividing member is first inserted into the enclosure. Then the osmotic agent or agents are inserted into the enclosure, and the semipermeable membrane plug is inserted into the opening through which the dividing member and osmotic agents where inserted. Thereafter, if the osmotic delivery system enclosure includes two openings located opposite from each other, the system is rotated 180°, and the beneficial agent is inserted into the enclosure through the opening through which the delivery plug is to be inserted. After the desired amount of beneficial agent has been inserted into the enclosure, the delivery plug having the delivery port is then inserted into the opening through which the beneficial agent was inserted. The delivery plug effectively seals the enclosure from the exterior environment, except for the delivery port.

When the osmotic delivery system with the delivery plug is placed in the environment of use, liquid is imbibed through the semipermeable membrane plug by osmosis, causing the osmotic agent to expand and causing the beneficial agent to flow through the delivery port in the delivery plug. Thus, the beneficial agent exits the enclosure of the osmotic delivery system through the delivery port, and is delivered to the environment of use.

One problem associated with the above-described osmotic delivery system, is that air or gas is frequently trapped above the beneficial agent as the delivery plug is inserted into the osmotic delivery system enclosure. When liquid begins to be imbibed by the osmotic agent through the membrane plug, the osmotic agent expands and drives the dividing member, compressing the beneficial agent to be delivered through the delivery port. Because of air pockets trapped in the compartment or within the beneficial agent formulation itself, the osmotic pressure must compress the air pockets before the incompressible beneficial agent will be delivered through the delivery channel in the delivery plug. This is problematic because the start-up period to delivery of the beneficial agent is delayed by the amount of time during which the air pockets are compressed. The time to "start-up" of delivery generally refers to the time from insertion into the environment of use until the beneficial agent is actually delivered at a rate not less than approximately 70% of the intended steady-state rate. The start-up period may be delayed up to several days or weeks, depending upon the size of the air gaps and the flow rate of the system. Delayed start-up of beneficial agent delivery is a significant problem in osmotic delivery systems. Furthermore, air might be expelled from the osmotic delivery system and cause serious health risks to, for example, humans having implanted osmotic delivery systems, depending on where the system is implanted.

If the osmotic delivery system includes a delivery plug with a very small delivery path or channel, the trapped air may completely prevent the flow of beneficial agent from the delivery channel and/or cause the beneficial agent to be delivered in sporadic bursts.

Another problem associated with the above-described osmotic delivery system is that surplus beneficial agent is typically expelled from the enclosure when the delivery plug is inserted into the enclosure which contains the beneficial agent. Surplus beneficial agent is necessary to ensure that as much air as possible escapes the delivery enclosure. This expelled beneficial agent must be cleaned from the osmotic delivery system enclosure, and makes it difficult to precisely determine the amount of beneficial agent within the osmotic delivery system and the amount of beneficial agent eventually delivered. This wasted agent problem is even more dramatic because most beneficial agents are extremely expensive, and the surplus agent cannot be recovered for re-use. In some instances, as much as forty microliters of beneficial agent may be expelled during the insertion process.

The delivery channel or orifice in the delivery plug which has been inserted in the above-described osmotic delivery systems is the site of interaction between the beneficial agent and the external environment of use. One constraint of certain delivery paths of known delivery plugs is that they must be small enough, either in length and/or interior cross-sectional area, such that the average velocity of active agent out of the delivery system enclosure is higher than the inward flow of liquid into the delivery system from the environment of use. Thus, these delivery channels or orifices in the delivery plug serve the important function of isolating the beneficial agent from liquids and particulate in the external environment of use, since any contamination of the beneficial agent by such external substances may adversely affect the utility of the beneficial agent. For example, the inward flux of materials from the environment of use due to diffusion through the delivery orifice may contaminate the interior of the capsule, destabilizing, diluting, or otherwise altering the beneficial agent formulation. It has been particularly problematic to prevent the diffusion of liquids from the environment of use through the delivery orifice of known osmotic delivery systems such that the utility of the beneficial agent is not impaired, while also obtaining the desired delivery rate of beneficial agent from the osmotic delivery system.

Still another problem associated with the above-described osmotic delivery system is that after the delivery plug has been inserted into the enclosure of the osmotic delivery system, the end of the system with the delivery plug inserted therein must be capped. This capping process is necessary to prevent the beneficial agent from evaporating through the delivery channel or orifice in the delivery plug during the period of time before the osmotic delivery system is inserted into its environment of use. Thus, during the implantation procedure, the cap must be removed prior to implantation of the unit, further complicating the implantation process and the assembly process of the osmotic delivery system.

Because of the above-identified problems associated with current osmotic delivery systems, it is costly and particularly difficult to administer beneficial agents from osmotic delivery systems at controlled delivery rates.

SUMMARY OF THE INVENTION

A primary object of the present invention is to provide an osmotic delivery system flow modulator assembly which enhances performance of osmotic delivery systems.

Another object of the present invention is to provide an osmotic delivery system flow modulator assembly which can reduce the start-up time before delivery of the beneficial agent from an osmotic delivery system.

Still another object of the present invention is to provide an osmotic delivery system flow modulator assembly which simplifies the assembly of osmotic delivery systems.

Another object of the present invention is to provide an osmotic delivery system flow modulator assembly which reduces back diffusion of substances from the external environment into the osmotic delivery system.

Yet another object of the present invention is to provide an osmotic delivery system which has a reduced start-up time as compared to conventional osmotic delivery systems.

Another object of the present invention is to provide an osmotic delivery system that does not require a cap on the osmotic delivery system after assembly to prevent beneficial agent evaporation from the system.

Another object of the present invention is to provide a method of assembling an osmotic delivery system which reduces the amount of wasted beneficial agent.

Still another object of the present invention is to provide a method of assembling an osmotic delivery system which reduces the possibility of gas or air trapped therein.

Another object of the present invention is to provide a method of delivering a beneficial agent into an osmotic delivery system which permits air or gas to escape the enclosure of the osmotic delivery system while the beneficial agent is delivered into the enclosure.

The present invention addresses the disadvantages of known osmotic delivery systems by providing embodiments of an osmotic delivery system flow moderator or modulator body, an osmotic delivery system flow modulator assembly, an osmotic delivery system incorporating the flow modulator assembly, a method of assembling an osmotic delivery system, and a method of delivering a beneficial agent into an osmotic delivery system. As used herein, "modulator" and "moderator" are used interchangeably. The osmotic delivery system flow modulator body or assembly reduces the occurrence of air pockets within the beneficial agent or between the beneficial agent and the flow modulator, reduces the amount of beneficial agent wasted when assembling the delivery system, and, according to another embodiment of a flow modulator assembly, minimizes the back diffusion of substances from the external environment of use.

According to one aspect of the present invention, an osmotic delivery system includes a semipermeable portion, and an enclosure having an opening and an interior for holding a liquid swellable osmotic agent and a beneficial agent. The liquid swellable osmotic agent imbibes liquid from a surrounding environment through the semipermeable portion to cause delivery of the beneficial agent from the enclosure. Also included is an osmotic delivery system flow modulator body at least partially positioned in the opening of the enclosure. The body has two opposing ends and means for venting the osmotic delivery system when the beneficial agent is inserted into the osmotic delivery system. A delivery path is located separate from the venting means, and is for delivering the beneficial agent from the osmotic delivery system. The delivery path is formed in at least one of the enclosure and the body.

According to another aspect of the present invention, an osmotic delivery system flow modulator assembly includes a flow modulator body constructed and arranged for at least partial positioning in an opening of an enclosure of an osmotic delivery system. The body includes two opposing ends, and a vent hole located through the body communicates the opposing ends. A delivery path is formed in the body, and is located separate from the hole for delivering a beneficial agent from the osmotic delivery system.

According to another aspect of the present invention, an osmotic delivery system flow modulator assembly includes a flow modulator body constructed and arranged for at least partial positioning in an opening of an enclosure of an osmotic delivery system. The body includes two opposing ends, a first hole located through the body, and a second hole located through the body. The first hole and the second hole each communicate the opposing ends. The flow modulator body includes a delivery path for delivering a beneficial agent from the osmotic delivery system. The flow modulator assembly includes means for sealing at least one of the first and second holes.

According to another aspect of the present invention, an osmotic delivery system includes a semipermeable portion and an enclosure having an opening and an interior for holding a liquid swellable osmotic agent and a beneficial agent. The liquid swellable osmotic agent imbibes liquid from a surrounding environment through the semipermeable portion to cause delivery of the beneficial agent from the enclosure. The delivery system includes an osmotic delivery system flow modulator assembly having a body at least partially positioned in the opening of the enclosure. The body has two opposing ends, a first hole located through the body, and a second hole located through the body. The first and second holes each communicate the opposing ends. The flow modulator assembly includes at least one cap positioned in one of the first and second holes, and at least one of the body and the enclosure include a delivery path for delivering a beneficial agent from the osmotic agent delivery system.

According to another aspect of the present invention, an osmotic delivery system flow modulator assembly includes a body constructed and arranged for at least partial positioning in an opening of an enclosure of an osmotic delivery system. The body has two opposing ends, and a hole located through the body. The hole communicates the opposing ends. The body has a delivery path for delivering a beneficial agent from the osmotic delivery system. A stopper has a head, a shaft, and a tip located opposite from the head. The stopper is at least partially positioned in the hole to seal the hole, and a partition secured to the body with the stopper so that the partition is secured between the body and the head of the stopper.

According to another aspect of the present invention, an osmotic delivery system includes a semipermeable portion, and an enclosure having an opening and an interior for holding a liquid swellable osmotic agent and a beneficial agent. The liquid swellable osmotic agent imbibes liquid from a surrounding environment through the semipermeable portion to cause delivery of the beneficial agent from the enclosure. An osmotic delivery system flow modulator body is at least partially positioned in the opening of the enclosure. The body has two opposing ends, and a hole located through the body communicating the opposing ends. A delivery path is located separate from the hole and formed in at least one of the body and the enclosure for delivering the beneficial agent from the osmotic delivery system. Also included are means for substantially preventing a liquid external from the osmotic delivery system from entering the interior of the osmotic delivery system. The preventing means allows the beneficial agent to exit the osmotic delivery system to the surrounding environment.

According to another aspect of the present invention, a method of assembling an osmotic delivery system includes the steps of: positioning an osmotic agent in an interior of the enclosure; inserting an osmotic delivery system flow modulator body at least partially in the opening of the enclosure to at least partially seal the opening, one of the flow modulator body and the enclosure having a delivery path for delivering a beneficial agent from the osmotic delivery system; and delivering a beneficial agent into the enclosure through a fill hole in the flow modulator body.

According to another aspect of the present invention, a method of delivering a beneficial agent into an osmotic delivery system includes the steps of inserting the beneficial agent through a hole in a flow modulator body inserted in an opening of the osmotic delivery system, and venting a gas from the osmotic delivery system through the hole while inserting the beneficial agent through the hole.

According to another aspect of the present invention, a method of assembling an osmotic delivery system includes the steps of positioning an osmotic agent into an interior of the enclosure; inserting an osmotic delivery system flow modulator body at least partially in the opening of the enclosure, the flow modulator body having a hole and a delivery path located separate from the hole; delivering a beneficial agent into the enclosure through the hole in the flow modulator body; and creating a vacuum adjacent to the flow modulator body to reduce an amount of gas within the osmotic delivery system.

Still other objects and advantages of the present invention will become readily apparent to those skilled in the art from the following detailed description, which illustrates and describes the preferred embodiment of the present invention. As will be realized, the invention is capable of modification in various obvious aspects, all without departing from the invention. Accordingly, the drawings and description are to be regarded as illustrative in nature, and not restrictive.

BRIEF DESCRIPTION OF THE DRAWINGS

The invention will be described in greater detail with reference to the accompanying drawings in which like elements bear like reference numerals, and wherein:

FIG. 7 is a cross-sectional side view of an osmotic delivery system flow modulator according to one embodiment of the present invention.

FIG. 8 is a cross-sectional side view of an osmotic delivery system flow modulator according to one embodiment of the present invention.

DESCRIPTION OF THE PREFERRED EMBODIMENT

Figure 1:
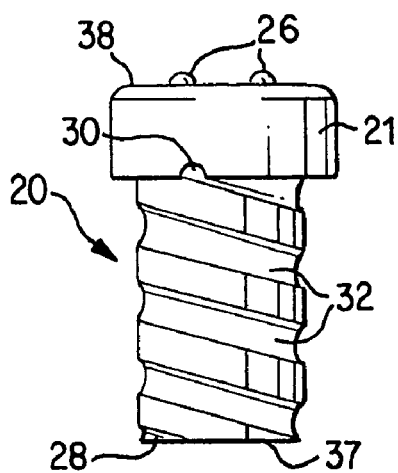
FIG. 1 is a side view of an osmotic delivery system flow modulator according to one embodiment of the present invention.
Figure 6:
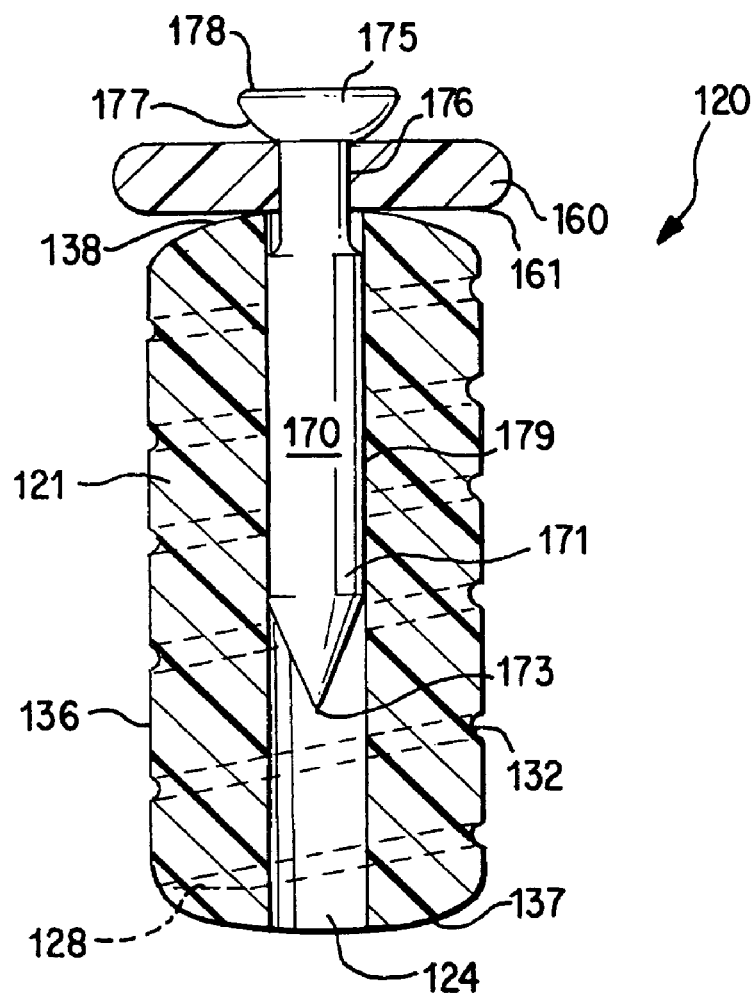
FIG. 6 is a cross-sectional side view of the osmotic delivery system flow modulator according to one embodiment of the present invention taken along the line 6-6 of FIG. 5.

The present invention relates to osmotic delivery system flow modulator assemblies which enhance the start-up and performance of osmotic delivery systems which incorporate the flow modulator. FIGS. 1, 6, and 8 illustrate osmotic delivery system flow modulator assemblies 20, 120, 220 according to embodiments of the present invention. The osmotic delivery system flow modulator assemblies 20, 120, 220 will be described in reference to exemplary osmotic delivery systems 40, 140, 240 according to embodiments of the present invention. The osmotic delivery systems 40, 140, 240 include the respective flow modulator assemblies 20, 120, 220.

The osmotic delivery system flow modulator assemblies 20, 120, 220 include a flow modulator body 21, 121, 221 having venting means or holes 24, 124, 224 located through the bodies of the flow modulator assemblies and communicating the opposing ends of the bodies. The flow modulator body 21 also includes a second, additional hole or fill hole 22 also communicating the two opposing ends 37, 38. The osmotic delivery system flow modulator assemblies 20, 120, 220 lessen the chance that air or gas pockets will form in the enclosures 42, 142, 242 of the osmotic delivery systems 40, 140, 240 during assembly of the system, specifically during the delivery of the beneficial agent 44, 144, 244 into the enclosure of the system through the holes 22, 124, 224. Because use of the osmotic delivery system flow modulator assemblies 20, 120, 220 with the osmotic delivery systems 40, 140, 240 lessens the chance of air or gas formations within the enclosures 42, 142, 242, the time to start-up of delivery of the beneficial agent 44, 144, 244 and performance of the system is enhanced. Use of the flow modulator assemblies 20, 120, 220 also lessens the chance that beneficial agent 44, 144, 244 will be wasted during assembly of the osmotic delivery systems 40, 140, 240.

FIG. 1 illustrates a side view of the exemplary osmotic delivery system flow modulator assembly 20. The body 21 of the flow modulator assembly 20 is constructed and arranged for at least partial positioning in the second opening 39 of the enclosure 42. The flow modulator body 21 illustrated in FIGS. 1-4 is generally cylindrically shaped, and is intended for insertion or positioning into the second opening 39 of the enclosure 42 of the exemplary osmotic delivery system 40. Because the enclosure 42 and opening 39 therein are cylindrical, the flow modulator body 21 is also cylindrical such that it is at least partially positionable in the second opening of the enclosure. Of course, the flow modulator body 21 may be other different shapes and sizes, which generally correspond to that of the second opening 39 in the enclosure 42 of the osmotic delivery system 40, such that the body 21 of the flow modulator assembly 20 is constructed and arranged for at least partial positioning in the opening. For example, if the second opening 39 of the enclosure 42 were square, the flow modulator would also be configured in a square shape.

The osmotic delivery system flow modulator body 21 is formed from an inert and, preferably, biocompatible material. Exemplary biocompatible and inert materials include, but are not limited to, metals such as titanium, stainless steel, platinum and their alloys, and cobalt-chromium alloys and the like. Other compatible materials include polymers such as polyethylene, polypropylene, polycarbonate, polymethylmethacrylate, and the like.

As illustrated in FIG. 1, the flow modulator body 21 of the osmotic delivery system flow modulator assembly 20 may include the delivery path 32. In the embodiment of the present invention illustrated in FIG. 1, the delivery path 32 is helical shaped. This helical delivery path 32 permits the beneficial agent 44 located within the enclosure 42 of the osmotic delivery system 40 to travel from the interior of the enclosure to the exterior environment of use. The helical delivery path 32 is formed between the threads 36 which are located on the elongated portion of the osmotic delivery system flow modulator body 21.

Once the flow modulator body 21 is inserted into the second opening 39 of the enclosure 42 above the beneficial agent 44, the interior surface 43 or wall of the enclosure will abut against the threads 36 such that the only area through which the beneficial agent may travel is the delivery path 32 formed between the threads. So configured, the helical delivery path 32 begins at the delivery entrance 28 which intersects the first opposing end 37, and ends at the delivery orifice 30. Once the osmotic agent 47 generates osmotic pressure within the delivery system, the beneficial agent 44 within the enclosure 42 will travel into the delivery entrance 28, flow along the helical delivery path 32, and finally exit the delivery orifice 30 to the environment of use.

The pitch, the amplitude, cross-sectional area, and the shape of the helical path 32 formed between the abutting surfaces of the threads 36 and the interior surface 43 of the enclosure 42 are factors that affect both the back pressure within the osmotic delivery system 40 and the possibility of back diffusion through the delivery path 32. In general, the geometry of the delivery path 32 is such that it reduces back diffusion of liquid from the environment of use into the enclosure 42. However, as further described below, a flow modulator assembly 120 according to another embodiment of the present invention may be used to mechanically minimize back flow or back diffusion. The geometry of the osmotic delivery system flow modulator body 21 illustrated in FIG. 1 is such that the length of the helical flow path 32 and the velocity of flow of beneficial agent 44 therethrough is sufficient to prevent back diffusion of external liquid through the flow path 32 without significantly increasing the back pressure within the enclosure 42. Thus, following start-up of the osmotic delivery system 40, the release rate of the beneficial agent 44 is governed by the osmotic pumping rate of the system. Factors to be considered in sizing the delivery path 32 are disclosed in U.S. patent application Ser. No. 08/595,761, the entire disclosure of which is incorporated herein by reference.

The size of the flow modulator body 21 is such that a seal is formed between the interior surface 43 of the enclosure 42 and the outer surface of the threads 36 on the flow modulator body 21. The seal formed between the modulator 20 and the enclosure 42 preferably may withstand the maximum osmotic pressure generated within the osmotic delivery system 40, or to fail safe if the pressure within the system exceeds a predetermined threshold. In the embodiment of the present invention depicted in FIGS. 1-4, the flow modulator fits tightly into the second opening 39 of the enclosure 42, forming a seal between the threads 36 of the body 21 and the inner surface 43 of the enclosure. However, the seal may be formed by other techniques well known in the art.

The delivery path 32 of the beneficial agent 44 is formed between the threads 36 of the modulator 20 and the enclosure 42. The delivery path length, interior cross-sectional shape, and area of the path are chosen such that the average linear velocity of the beneficial agent 44 through the path is higher than that of the linear inward flux of materials in the environment of use due to diffusion or osmosis, thereby attenuating or moderating back diffusion and its deleterious effects of contaminating the interior of the osmotic delivery system 40, destabilizing, diluting, or otherwise altering the beneficial agent formulation. The release rate of the beneficial agent 44 can be modified by modifying the delivery pathway 32 geometry, as described below.

The convective flow of beneficial agent 44 out of the delivery orifice 30 is set by the pumping rate of the osmotic delivery system 40 and the concentration of beneficial agent in the enclosure 42, which can be represented as follows:

$$Q_{ca} = (Q)(C_a) \quad (1)$$

where $Q_{ca}$ is the convective transport of beneficial agent 44 in mg/day

Q is the overall convective transport of the beneficial agent formulation in cm$^3$/day $C_a$ is the concentration of beneficial agent 44 in the formulation within enclosure 42 in mg/cm$^3$ The diffusive flow of agent 44 through the delivery orifice 30 is a function of agent concentration, cross-sectional configuration of delivery path 32, agent diffusivity, and length of delivery path, which can be represented as follows:

$$Q_{da} = D\pi r^2 \Delta C_a / L \quad (2)$$

where $Q_{da}$ is the diffusive transport of agent 44 in mg/day

D is the diffusivity through the delivery path 32 in cm$^2$/day r is the effective inner radius of the delivery path in cm $C_a$ is the difference between the concentration of beneficial agent 44 in the enclosure 42 and in the environment of use outside of the delivery orifice 30 in mg/cm$^3$ L is the length of the delivery path in cm In general, the concentration of beneficial agent 44 in the enclosure 42 is much greater than the concentration of agent in the environment of use such that the difference, $C_a$ can be approximated by the concentration of agent within the enclosure, $C_a$. Thus:

$$Q_{da} = D\pi r^2 C_a / L \quad (3)$$

It is generally desirable to keep the diffusive flux of agent at less than 10% of the convective flow. This is represented as follows:

$$Q_{da}/Q_{ca} = D\pi r^2 C_a / QC_a L = D\pi r^2 / QL \leq 0.1 \quad (4)$$

Equation 4 indicates that the relative diffusive flux decreases with increasing volumetric flow rate and path length, increases with increasing diffusivity and channel radius, and is independent of beneficial agent concentration.

The diffusive flux of water where the orifice 30 opens into the enclosure 42 can be approximated as:

$$Q_{wd}(res) = C_O Q e^{(-QL/D_w A)} \quad (5)$$

where $C_o$ is the concentration profile of water in mg/cm$^3$

Q is the mass flow rate in mg/day

L is the length of the delivery path in cm $D_w$ is the diffusivity of water through the material in the delivery path in cm$^2$/day A is the cross-sectional area in the delivery path in cm$^2$ The hydrodynamic pressure drop across the delivery orifice can be calculated as follows:

$$\Delta P = \frac{8QL\mu}{\pi r^4} \quad (6)$$

Simultaneously solving equations (4), (5), and (6) gives the values shown in Table I for a series of different effective delivery orifice diameters where:

Q=0.38 μl/day $C_a$=0.4 mg/μl

L=5 cm $D_a$=2.00 E−06 cm$^2$/sec

μ=5.00 E+02 cp $C_{wo}$=0 mg/μl $D_w$=6.00 E+06 cm$^2$/sec

TABLE 1

| | | Drug Diffusion & Pumping | | | | | |
|---|---|---|---|---|---|---|---|
| Effective | Cross Sec | Pump Rate | Diffusion | | Water Intrusion | | Pressure |
| Orifice dia (mil) | area (mm$^2$) | $Q_{ca}$ mg/day | $Q_{da}$ mg/day | Diff/Conv $Q_{da}/Q_{ca}$ | $Q_{dw}$ mg/day | $Q_{dw}$ mg/year | Drop delta P psi |
| 1 | 0.00051 | 0.152 | 0.0001 | 0.0005 | 0 | 0 | 1.55800 |
| 2 | 0.00203 | 0.152 | 0.0003 | 0.0018 | 1.14E−79 | 4.16-E−77 | 0.09738 |
| 3 | 0.00456 | 0.152 | 0.0006 | 0.0041 | 4.79E−36 | 1.75E−33 | 0.01923 |
| 4 | 0.00811 | 0.152 | 0.0011 | 0.0074 | 8.89E−21 | 3.25E−18 | 0.00609 |
| 5 | 0.01267 | 0.152 | 0.0018 | 0.0115 | 1.04E−13 | 3.79E−11 | 0.00249 |
| 6 | 0.01824 | 0.152 | 0.0025 | 0.0166 | 7.16E−10 | 2.61E−07 | 0.00120 |
| 7 | 0.02483 | 0.152 | 0.0034 | 0.0226 | 1.48E−07 | 5.4E−05 | 0.00065 |
| 8 | 0.03243 | 0.152 | 0.0045 | 0.0295 | 4.7E−06 | 0.001715 | 0.00038 |
| 9 | 0.04105 | 0.152 | 0.0057 | 0.0373 | 5.04E−05 | 0.018381 | 0.00024 |
| 10 | 0.05068 | 0.152 | 0.0070 | 0.0461 | 0.000275 | 0.100263 | 0.00016 |
| 11 | 0.06132 | 0.152 | 0.0085 | 0.0558 | 0.000964 | 0.351771 | 0.00011 |
| 12 | 0.07298 | 0.152 | 0.0101 | 0.0664 | 0.002504 | 0.913839 | 0.00008 |
| 13 | 0.08564 | 0.152 | 0.0118 | 0.0779 | 0.005263 | 1.921027 | 0.00005 |
| 14 | 0.09933 | 0.152 | 0.0137 | 0.0903 | 0.00949 | 3.463836 | 0.00004 |
| 15 | 0.11402 | 0.152 | 0.0158 | 0.1037 | 0.015269 | 5.573195 | 0.00003 |
| 16 | 0.12973 | 0.152 | 0.0179 | 0.1180 | 0.022535 | 8.225224 | 0.00002 |
| 17 | 0.14646 | 0.152 | 0.0202 | 0.1332 | 0.031114 | 11.35656 | 0.00002 |
| 18 | 0.16419 | 0.152 | 0.0227 | 0.1493 | 0.040772 | 14.88166 | 0.00001 |
| 19 | 0.18295 | 0.152 | 0.0253 | 0.1664 | 0.051253 | 18.70728 | 0.00001 |
| 20 | 0.20271 | 0.152 | 0.0280 | 0.1844 | 0.062309 | 22.7427 | 0.00001 |

In the embodiment of the flow modulator 20 illustrated in FIG. 1, the delivery path 32 may be between about 0.5 and 20 cm long, preferably between about 1 and 10 cm long and between about 0.001 and 0.020 inches in diameter, preferably between about 0.003 and 0.015 inches to allow for a flow of between about 0.02 and 50 μl/day, usually 0.2 to 10 μl/day and often 0.2 to 2.0 μl/day. Additionally, a catheter or other system may be attached to the end of the flow modulator delivery orifice 30 to provide for delivery of the beneficial agent formulation at a site removed from the implantable osmotic delivery system. Such systems are known in the art and are described, for example, in U.S. Pat. Nos. 3,732,865 and 4,340,054, the disclosures of which are incorporated herein by reference.

Although preferred, the delivery path 32 need not be formed in the exterior surface of the flow modulator body 21. The flow modulator body 21 need not have the delivery path 32. For example, the interior surface 43 of the cylindrical enclosure 42 may include threads of a predetermined pitch, amplitude, and cross-sectional area. Such threads formed within the interior surface 43 of the enclosure 42 may function as the delivery path 32 for the beneficial agent 44. In such an embodiment, the flow modulator body 21 may have a smooth cylindrical outer surface which seals the second opening 39 in the enclosure 42, except for the delivery path 32 formed in the interior surface 43 of the enclosure. In such an embodiment, the flow modulator assembly 20 will continue to modulate flow because the outer surface continues to define the cross-sectional area of the delivery path 32. Alternatively, the interior surface 43 of the enclosure 42 and the outer cylindrical surface of the flow modulator body 21 each may have female threads, male threads, or any combination thereof to form a delivery path 32 of predetermined size. Furthermore, the delivery path 32 need not be a single helically shaped channel, it may be a straight or curved channel or series of channels.

Figure 3:
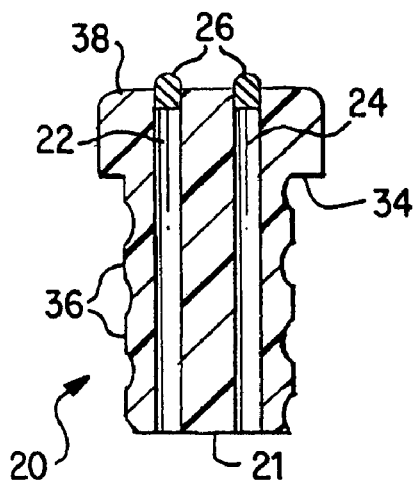
FIG. 3 is a cross-sectional side view of the osmotic delivery system flow modulator according to one embodiment of the present invention taken along the line 3-3 of FIG. 2.

As illustrated in FIG. 3, the exemplary osmotic delivery system flow modulator assembly 20 includes a first hole or vent hole 24 and a second, additional hole or fill hole 22. The vent hole 24 and the fill hole 22 are elongated, straight, and run longitudinally and parallel through the body 21 of the osmotic delivery system flow modulator assembly 20. In other words, the longitudinal axis of the fill hole 22 and the longitudinal axis of the vent hole 24 are substantially perpendicular to at least one of the opposing ends 37, 38 of the flow modulator. Because the flow modulator body 21 is preferably cylindrical such that it is constructed and arranged for at least partial positioning in the second opening 39 of the cylindrical enclosure 42, the vent hole 24 and fill hole 22 are parallel with the interior surface 43 and cylindrical outer surface of the enclosure 42.

Figure 2:
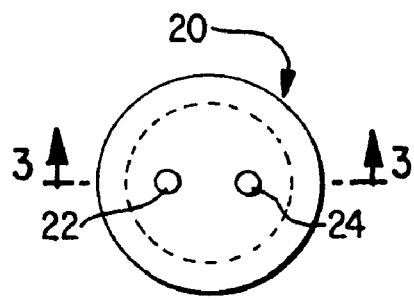
FIG. 2 is an end view of an osmotic delivery system flow modulator according to one embodiment of the present invention.

The vent hole 24 and the fill hole 22 run or extend completely through the body of the flow modulator, and communicate the first opposing end 37 with the second opposing end 38 of the cylindrical flow modulator body 21. As illustrated in FIG. 2, the vent hole 24 and the fill hole 22 each have a circular cross-sectional shape of the same diameter. Although the cross-sectional shape of the vent hole 24 and the fill hole 22 is preferably circular, other shapes for the holes are contemplated. For example, square, triangular, or oval cross-sectional shaped holes 22, 24 would all be within the confines of the present invention. Furthermore, the longitudinal axis of the holes 22, 24 need not be parallel with the longitudinal axis of the flow modulator body 21. For example, the holes 22, 24 may be located at an angle with respect to the longitudinal axis of the modulator body 21, or spiral through the flow modulator body 21.

The flow modulator assembly 20 is best described in reference to the osmotic delivery system 40 according to another embodiment of the present invention.

Figure 4:
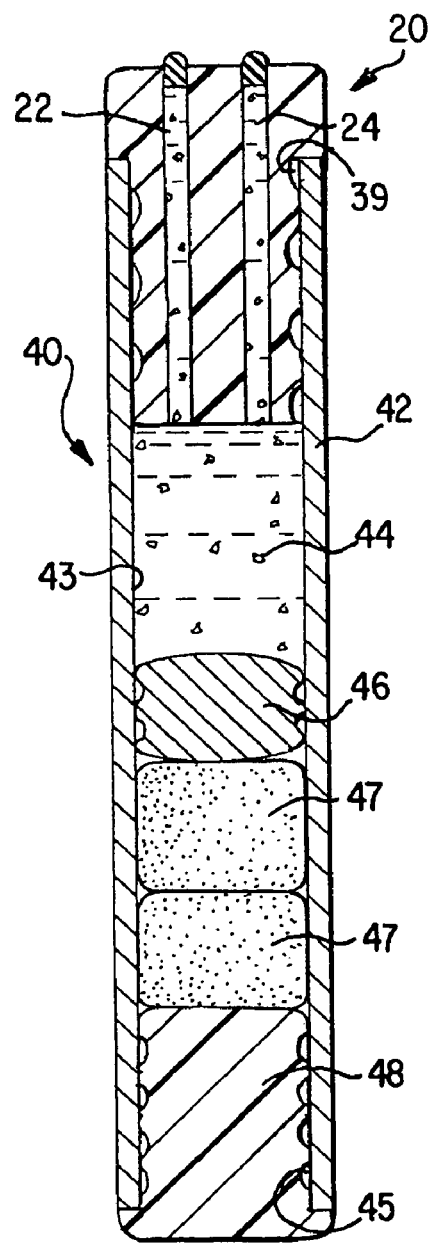
FIG. 4 is a cross-sectional side view of an osmotic delivery system according to one embodiment of the present invention.

FIG. 4 illustrates an example of an osmotic delivery system 40 according to the present invention. The configuration illustrated in FIG. 4 is one example of an osmotic delivery device and is not to be construed as limiting the present invention. The present invention is generally applicable to all osmotic delivery devices having any number of shapes, and to all such devices administered in any variety of methods such as oral, ruminal, and implantable osmotic delivery techniques.

The osmotic drug delivery system 40, as illustrated in FIG. 4, includes an elongated substantially cylindrical enclosure 42 having a second opening 39 for receiving the osmotic delivery system flow modulator 20, and a first opening 45 located opposite the flow modulator opening or second opening 39 for receiving the semipermeable plug 48. The delivery orifice 30 of the osmotic delivery system flow modulator assembly 20 is for delivering the beneficial agent 44 from the osmotic delivery system 40.

The elongated and cylindrical enclosure 42 is formed of a material which is sufficiently rigid to withstand expansion of the osmotic agent 47 without changing size or shape. The elongated enclosure 42 is preferably substantially impermeable to fluids in the environment of use as well as to ingredients contained within the delivery system 40 such that the migration of such materials into or out of the system through the impermeable material is so low as to have substantially no adverse impact on the function of the osmotic delivery system.

Materials which may be used for the enclosure 42 must be sufficiently strong to ensure that the enclosure will not leak, crack, break, or distort under stresses to which it would be subjected during implantation or under stresses due to the pressures generated during operation. The enclosure 42 may be formed of chemically inert and biocompatible, natural or synthetic materials which are known in the art. The enclosure material is preferably a non-bioerodible material which remains in the patient after use, such as titanium. However, the material of the enclosure may alternatively be a bioerodible material which bioerodes in the environment after dispensing of the beneficial agent. Generally, preferred materials for the enclosure 42 are those acceptable for human implantation.

In general, typical materials of construction suitable for the enclosure 42 according to the present invention include non-reactive polymers or biocompatible metals or alloys. The polymers include acrylonitrile polymers such as acrylonitrile-butadiene-styrene terpolymer, and the like; halogenated polymers such as polytetraflouroethylene, polychlorotrifluoroethylene, copolymer tetrafluoroethylene and hexafluoropropylene; polyimide; polysulfone; polycarbonate; polyethylene; polypropylene; polyvinylchloride-acrylic copolymer; polycarbonate-acrylonitrile-butadiene-styrene; polystyrene; and the like. Metallic materials useful for the enclosure 42 include stainless steel, titanium, platinum, tantalum, gold, and their alloys, as well as gold-plated ferrous alloys, platinum-plated ferrous alloys, cobalt-chromium alloys and titanium nitride coated stainless steel.

An enclosure 42 made from the titanium or a titanium alloy having greater than 60%, often greater than 85% titanium is particularly preferred for the most size-critical applications, for high payload capability and for long duration applications, and for those applications where the formulation is sensitive to body chemistry at the implantation site or where the body is sensitive to the formulation. In certain embodiments, and for applications other than the fluid-imbibing devices specifically described, where unstable beneficial agent formulations are in the enclosure 42, particularly protein and/or peptide formulations, the metallic components to which the formulation is exposed must be formed of titanium or its alloys as described above. Within the enclosure 42 is a beneficial agent 44 to be delivered. Such a beneficial agent 44 may optionally include pharmaceutically acceptable carriers and/or additional ingredients such as anti-oxidants, stabilizing agents, permeation enhancers, etc.

The present invention applies to the administration of beneficial agents 44 in general, which include any physiologically or pharmacologically active substance. The beneficial agent 44 in the osmotic delivery system 40 may be any of the agents which are known to be delivered to the body of a human or an animal such as medicaments, vitamins, nutrients, or the like. The beneficial agent 44 may also be an agent which is delivered to other types of aqueous environments such as pools, tanks, reservoirs, and the like. Included among the types of agents which meet this description are biocides, sterilization agents, nutrients, vitamins, food supplements, sex sterilants, fertility inhibitors and fertility promoters.

Drug agents which may be delivered by the present invention include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, anti-inflammatory corticosteroids, ocular drugs and synthetic analogs of these species.

Examples of drugs which may be delivered by devices according to this invention include, but are not limited to prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranitrate, digoxin, isoflurophate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-S-estradiol, ethinyl estradiol, ethinyl estradiol 3-methyl ether, prednisolone, 17α-hydroxyprogesterone acetate, 19-nor-progesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, capropril, mandol, quanbenz, hydrochlorothiazide, ranitidine, flurbiprofen, fenufen, fluprofen, tolmetin, alclofenac, mefenamic, flufenamic, difuinal, nimodipine, nitrendipine, nisoldipine, nicardipine, felodipine, lidoflazine, tiapamil, gallopamil, amlodipine, mioflazine, lisinolpril, enalapril, enalaprilat, captopril, ramipril, famotidine, nizatidine, sucralfate, etintidine, tetratolol, minoxidil, chlordiazepoxide, diazepam, amitriptyline, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatotropin, oxytocin, vasopressin, GRF, prolactin, somatostatin, lypressin, pancreozymin, luteinizing hormone, LHRH, LHRH agonists and antagonists, leuprolide, interferons, interleukins, growth hormones such as human growth hormone, bovine growth hormone and porcine growth hormone, fertility inhibitors such as the prostaglandins, fertility promoters, growth factors, coagulation factors, human pancreas hormone releasing factor, analogs and derivatives of these compounds, and pharmaceutically acceptable salts of these compounds, or their analogs or derivatives.

The beneficial agent 44 can be present in this invention in a wide variety of chemical and physical forms, such as solids, liquids and slurries. On the molecular level, the various forms may include uncharged molecules, molecular complexes, and pharmaceutically acceptable acid addition and base addition salts such as hydrochlorides, hydrobromides, sulfate, laurylate, oleate, and salicylate. For acidic compounds, salts of metals, amines or organic cations may be used. Derivatives such as esters, ethers and amides can also be used. A beneficial agent 44 can be used alone or mixed with other beneficial agents.

The enclosure 42 receives the osmotic agent 47, which in the embodiment of the present invention depicted in FIG. 4 is two osmotic tablets. Osmotic agents 47, specifically the osmotic tablets illustrated in FIG. 4, drive the osmotic flow of the osmotic delivery system 40. However, the osmotic agent 47 need not be a tablet; it may be other conceivable shapes, textures, densities, and consistencies and still be within the confines of the present invention. For example, the osmotic agent 47 may be in the form of a powder. The osmotic tablet is preferably and initially non-flowable and solid, but upon insertion of the osmotic delivery system 40 into the environment of use, an external liquid permeates through the semipermeable plug 48, causing the osmotic tablets to assume a flowable form.

The embodiment of the present invention illustrated in FIG. 4 includes a dividing member 46, which may be movable or stationary within the enclosure 42. The osmotic agent 47 within the enclosure 42 is separated from the beneficial agent 44 by the dividing member 46. The dividing member 46 may be in the form of a slidable or movable partition or a stationary and stretchable partition member. The dividing member 46 is preferably movable and is formed from an impermeable resilient material that includes annular ring shape protrusions which form a seal with the inner surface 43 of the enclosure 42.

The dividing member 46 is a substantially cylindrical member which is configured to fit within the enclosure 42 in a sealing manner which also allows the dividing member to slide along the longitudinal direction of the enclosure. The dividing member 46 isolates the beneficial agent 44 from the environmental liquids that are permitted to enter enclosure 42 through the semipermeable plug 48 such that in use, at steady-state flow, the beneficial agent is expelled through the delivery orifice 30 at a rate corresponding to the rate at which liquid from the environment of use flows into the osmotic agent 47 through the semipermeable plug. As a result, the flow modulator assembly 20 and the beneficial agent 44 will be protected from damage and their functionality will not be compromised even if the enclosure 42 adjacent the osmotic agent becomes deformed.

The dividing member 46 is preferably made of a material that is of lower hardness than the enclosure 42 and will deform to fit the lumen of the enclosure to provide a fluid tight compression seal with the enclosure. The materials from which the dividing member 46 may be made are preferably elastomeric materials that are impermeable and include but are not limited to polypropylene, rubbers such as EPDM, silicone rubber, butyl rubber, and the like, and thermoplastic elastomers such as plasticized polyvinylchloride, polyurethanes, Santoprene®, C-flex TPE (Consolidated Polymer Technologies, Inc.), and the like. The dividing member 46 may be a self-loading or a compression-loaded design. Other materials suitable for the dividing member 46 are elastomeric materials including the non-reactive polymers listed above, as well as elastomers in general, such as polyurethanes and polyamides, chlorinated rubbers, styrene-butadiene rubbers, and chloroprine rubbers.

However, the present invention need not include the dividing member 46. In such an embodiment, the beneficial agent 44 and the osmotic agent 47 may be separated by an interface between the osmotic agent and the beneficial agent or the may together form a homogeneous mixture.

As illustrated in FIG. 4, the osmotic delivery system 40 includes the semipermeable membrane plug 48 which is inserted into the first opening 45 within the enclosure 42. The semipermeable membrane plug 48 allows liquid to pass from an environment of use into the enclosure 42 to cause the osmotic agent 47 to swell. The semipermeable material forming the plug 48 is largely impermeable to materials within the enclosure 42 and other ingredients within the environment of use. Materials from which the semipermeable membrane plug 48 may be fabricated are well known within the art. The semipermeable membrane plug 48 is of a lower hardness material and will conform to the shape of the enclosure 42 to produce a liquid-tight seal with the interior of the enclosure 42 upon wetting. Materials from which the semipermeable membrane plug 48 are made are those that are semipermeable, can conform to the shape of the enclosure 42 upon wetting, and adhere to the rigid interior surface 43 of the enclosure.

The polymeric materials from which the semipermeable plug 48 may be made vary based on the pumping rates and system configuration requirements, and include, but are not limited to, plasticized cellulosic materials, enhanced polymethylmethacrylates such as hydroxyethylmethacrylate (HEMA), and elastomeric materials such as polyurethanes and polyamides, polyether-polyamide copolymers, thermoplastic copolyesters, and the like.

The osmotic tablets are osmotic agents 47 which are liquid attracting agents used to drive the flow of the beneficial agent 44. The osmotic agent 47 may be an osmagent, an osmopolymer, or a mixture of the two. Species which fall within the category of osmagent, i.e., the non-volatile species which are soluble in water and create the osmotic radiant driving the osmotic inflow of water, vary widely. Examples are well known in the art and include magnesium sulfate, magnesium chloride, potassium sulfate, sodium chloride, sodium sulfate, lithium sulfate, sodium phosphate, potassium phosphate, d-mannitol, sorbitol, inositol, urea, magnesium succinate, tartaric acid, raffinose, and various monosaccharides, oligosaccharides and polysaccharides such as sucrose, glucose, lactose, fructose, and dextran, as well as mixtures of any of these various species.

Species which fall within the category of osmopolymer are hydrophilic polymers that swell upon contact with water, and these vary widely as well. Osmopolymers may be of plant or animal origin, or synthetic, and examples of osmopolymers are well known in the art. Examples include: poly(hydroxyalkyl methacrylates) with molecular weight of 30,000 to 5,000,000, poly(vinylpyrrolidone) with molecular weight of 10,000 to 360,000, anionic and cationic hydrogels, polyelectrolyte complexes, poly(vinyl alcohol) having low acetate residual, optionally cross-linked with glyoxal, formaldehyde or glutaraldehyde and having a degree of polymerization of 200 to 30,000, a mixture of methyl cellulose, cross-linked agar and carboxymethylcellulose, a mixture of hydroxypropl methycellulose and sodium carboxymethylcellulose, polymers of N-vinyllactams, polyoxyethylene-polyoxypropylene gels, polyoxybutylene-polyethylene block copolymer gels, carob gum, polyacrylic gels, polyester gels, polyurea gels, polyether gels, polyamide gels, polypeptide gels, polyamino acid gels, polycellulosic gels, carbopol acidic carboxy polymers having molecular weights of 250,000 to 4,000,000, Cyanamer polyacrylamides, cross-linked indene-maleic anhydride polymers, Good-Rite polyacrylic acids having molecular weights of 80,000 to 200,000, Polyox Polyethylene oxide polymers having molecular weights of 100,000 to 5,000,000, starch graft copolymers, and Aqua-Keeps acrylate polymer polysaccharides.

In assembling the osmotic delivery device 40 according to one embodiment of the present invention, the movable dividing member 46 is first inserted into the first opening 45 of the enclosure 42. The osmotic agent 47 is then positioned or placed through the same first opening 43 such that it is adjacent to the movable dividing member 46. Thereafter, the semipermeable plug 48 is inserted into the same first opening 43, effectively sealing this opening. Thus, the osmotic agent 47 is adjacent to the semipermeable plug 48 and, preferably, in fluid communication with the semipermeable plug 48 such that fluids may flow through the semipermeable portion to the osmotic agent. The osmotic delivery system 40 is then preferably rotated such that the second opening 39 of the enclosure 42 located opposite the semipermeable plug 48 faces vertically upward.

In previous osmotic delivery systems, the beneficial agent is next measured and inserted into an opening of the system such that it is located above the dividing member. Ordinarily, the last step in assembling these systems is to insert a delivery plug into the this opening. However, the osmotic delivery system 40 according to one embodiment of the present invention includes the osmotic delivery system flow modulator assembly 20 illustrated in FIG. 4. The beneficial agent 44 may be delivered to the interior of the enclosure through the fill hole 22 in the flow modulator body 21.

Thus, when assembling the osmotic delivery system 40 according to the present invention, the flow modulator body 21 is first inserted at least partially into the second opening 39 of the enclosure 42 opposite the semipermeable plug 48 before the beneficial agent 44 is delivered into the system. The flow modulator body 21 is preferably inserted into the enclosure 42 such that the head surface 34 abuts against the enclosure 42. Thus, the head surface 34 controls the depth that the flow modulator may be inserted into the second opening 41 in the enclosure 42. The head surface 34 preferably extends perpendicularly from the longitudinal axis of the flow modulator body 21 such that it extends radially away from the threads 36. The delivery path 32, in the embodiment of the flow modulator assembly 20 depicted in FIG. 1, ends at the delivery orifice 30, which is located on or near the head surface 34.

Thereafter, a pipette, syringe, or other similar device, preferably filled with the beneficial agent 44, is arranged above or within the fill hole 22, and the beneficial agent is released into the fill hole at a predetermined rate, delivering the beneficial agent into the interior of the enclosure 42 through the fill hole. The fill hole 22 may be sized to matingly receive a fill tube of a syringe, or may also be larger than the diameter of the fill tube of the syringe such that the fill hole also permits venting like the vent hole 24. The predetermined rate of release of beneficial agent 44 from the pipette is such that a gas, such as air, within the beneficial agent or the enclosure 42 has the opportunity to escape through the vent hole 24 as the incoming beneficial agent is delivered through the fill hole 22 and fills the interior of the enclosure. Thus, it is apparent that the vent hole 24, and all of its possible configurations discussed above, acts as means for venting the osmotic delivery system 40 when the beneficial agent 44 is inserted into the osmotic delivery system. The beneficial agent 44 is delivered for a predetermined period of time such that the beneficial agent fills the enclosure 42, and at least partially fills the fill hole 22 and the vent hole 24. Finally, the caps 26, illustrated in FIG. 3 are inserted into the vent hole 24 and fill hole 22, capping or sealing the holes such that beneficial agent 44 located within the delivery system 40 will not escape from the enclosure 42, save from the delivery orifice 30.

The caps 26, or means for sealing the holes 22, 24 from the surrounding environment, may be fashioned from a material similar to that of the osmotic delivery system flow modulator body 21, and should sufficiently seal the fill hole 22 and vent hole 24 from the environment of use such that external liquids from the environment of use do not substantially leak or diffuse into the osmotic delivery system 40, and such that pressures generated from the osmotic agent 47 within the osmotic delivery system 40 do not substantially cause the beneficial agent 44 to leak out from the fill hole 22 or vent hole 24. The caps 26 may press fit or thread into the holes 22, 24. However, the fill hole 22 and vent hole 24 need not be sealed by the caps 26. Plugs, inserts, molten plastics, rods, and other devices or items may also be used to cap the fill hole 22 and the vent hole 24 such that they also function as means for sealing. Likewise, one cap may be used to cover and seal both holes 22, 24.

The fill hole 22 and the vent hole 24 are sized to accommodate the predetermined rate that beneficial agent 44 is delivered into the fill hole. If this delivery rate is relatively slow, the fill hole 22 may have a smaller diameter and/or a longer length. If the predetermined rate of delivery of beneficial agent 44 into the fill hole 22 is relatively fast, the fill hole 22 must have a larger diameter and/or a shorter length such that the beneficial agent does not overflow the fill hole 22 as it is delivered through the hole. The fill hole 22 may have sufficient volume to accommodate the rate of beneficial agent 44 delivered through the fill hole such that there is relatively little pressure drop across the fill hole during delivery of the beneficial agent through the fill hole.

Alternatively, the beneficial agent 44 may be forced into and through the fill hole 22 such that there is a significant pressure drop across the fill hole, which also forces air quickly out of the enclosure 42 through the vent hole 24.

The preferred size of the fill hole 22 is also dependent upon the size of the vent hole 24. Because the flow modulator forms a seal with the interior surface of the enclosure, the vent hole 24 should be sufficiently large to accommodate the rate of escaping air or gas from within the enclosure 42, which roughly equals the rate that beneficial agent 44 is pipetted into the fill hole 22, depending upon the amount of gas allowed to escape through the fill hole 22. Because air is compressible, the vent hole 24 may be smaller than the fill hole 22, yet accommodate the same rate of escaping air as entering beneficial agent 44. However, once the enclosure 42 is sufficiently full of beneficial agent 44 such that the agent begins to rise into the fill hole 22 and vent hole 24, the rate that the beneficial agent rises in the vent hole preferably matches that of the rising rate in the fill hole. Thus, the fill hole 22 and vent hole 24 preferably have the same volume, which in the embodiment of the present invention illustrated in FIG. 3, is obtained by matching the diameters and lengths of the cylindrical fill and vent holes.

However, if the flow moderator body 21 is made from a resilient material, the fill hole 22 and vent hole 24 must not be overly large such that the sealing capacity of the threads 36 against the interior surface 43 is compromised.

As shown in FIGS. 3 and 4, the fill hole 22 and the vent hole 24 are preferably located separate from the delivery path 32 such that the holes and the path are not integral. This is preferred because, although some venting may occur in the delivery path 32, it is typically too small to effectively vent the osmotic delivery system 40 without the assistance of a vacuum during the beneficial agent filling process.

Assembling the osmotic delivery system 40 in the above described manner is advantageous because the amount of wasted beneficial agent 44 is reduced. Beneficial agent 44 is preferably delivered into the enclosure 42 through the fill hole 22 until the fill hole and the vent hole 24 are both substantially filled with beneficial agent. Thereafter, the fill hole 22 and the vent hole 24 are capped with the caps 26. When the holes 22, 24 are capped with the caps 26, a minute amount of surplus beneficial agent 44 is expelled from the flow modulator. This reduced amount of beneficial agent expelled when assembling an osmotic delivery system 40, as compared to past assembly methods, reduces the costs of assembly. Because the amount of expelled and wasted beneficial agent is reduced, it is also easier to determine the precise amount of beneficial agent 44 remaining in the osmotic delivery system.

As described above, when delivering the beneficial agent 44 into the osmotic delivery system 40, the vent hole 24 permits gas within the enclosure of the osmotic delivery system to escape from the system. Thus, when the osmotic delivery system 40 is completely assembled, the amount of gas within the system is reduced. This reduction of trapped air or gas within the system 40 is advantageous because the time to start-up of delivery of beneficial agent 44 from the delivery system to the environment of use is reduced.

When the osmotic delivery system 40 is eventually placed into an environment of use, the osmotic agent 47 imbibes fluid through the semipermeable plug 48 and expands, creating osmotic pressure within the enclosure 42. This osmotic pressure forces the beneficial agent 44 through the delivery path 32. Because the amount of gas or air within the enclosure 42 is reduced during assembly of the osmotic delivery system 40, the osmotic agent 47 need not first compress air within the beneficial agent or interior of the delivery system before forcing the beneficial agent into the delivery entrance 28. Hence, the start-up period to delivery of the beneficial agent 44 is not delayed by the amount of time which would ordinarily be required to compress air pockets within the osmotic delivery system 40. Furthermore, the chance that significant amounts of air or gas may expel from the system, causing possible health risks, is reduced.

FIGS. 5-8 illustrate osmotic delivery system flow modulator assemblies 120, 220 according to further embodiments of the present invention. The osmotic delivery system flow modulator assemblies 120, 220 will be described in reference to exemplary osmotic delivery systems 140, 240 according to further embodiments of the present invention illustrated in FIGS. 7 and 8. Each of the osmotic delivery systems 140, 240 includes the respective flow modulator assemblies 120, 220. Features on the flow modulator assemblies 120, 220, and osmotic delivery systems 140, 240 that are similar to features on the flow modulator assembly 20 and osmotic delivery system 40 are assigned corresponding reference numbers, increased by 100's. Thus, the above description of the benefits and functions of the different components of the flow modulator assembly 20, osmotic delivery system 40, and methods of assembling associated therewith also apply to the flow modulator assemblies 120, 220 and osmotic delivery systems 140, 240. However, the flow modulator assemblies 120, 220 and the osmotic delivery systems 140, 240 include additional features and inherent functions, as described below.

Figure 5:
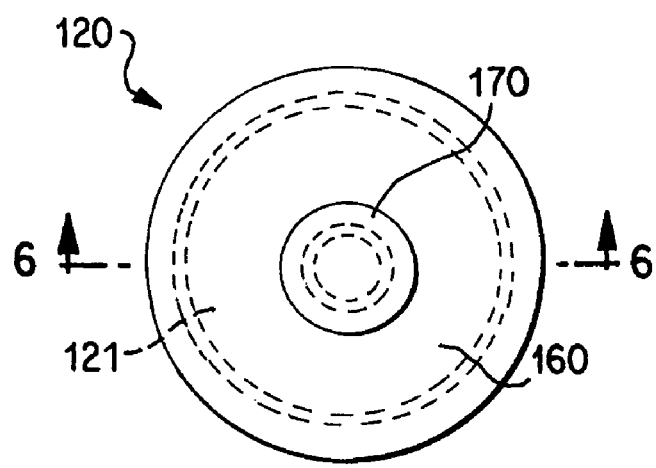
FIG. 5 is an end view of an osmotic delivery system flow modulator according to one embodiment of the present invention.

As shown in FIGS. 5 and 6, the osmotic delivery system flow modulator assembly 120 includes a flow modulator body 121 having a filling and venting hole 124 located through the body of the flow modulator and communicating the opposing ends 137, 138 of the body. The osmotic delivery system flow modulator assembly 120, similar to the osmotic delivery system flow modulator assembly 20, lessens the chance that air or gas pockets will form in the enclosure 142 of the osmotic delivery system 140 during assembly of the system, specifically during the delivery of the beneficial agent 144 into the enclosure of the system through the hole 124 in the flow modulator body 121. Because use of the osmotic delivery system flow modulator assembly 120 with the osmotic delivery system 140 lessens the chance of air or gas formations within the enclosure 142, the time to start up of delivery of the beneficial agent 144 and performance of the system is enhanced. Use of the flow modulator assembly 120 also lessens the chance that beneficial agent will be wasted during assembly of osmotic delivery system 140, and also reduces back diffusion of substances from the external environment into the osmotic delivery system.

FIGS. 5 and 6 illustrate an exemplary osmotic delivery system flow modulator assembly 120 according to one embodiment of the present invention. Like the osmotic delivery system flow modulator assembly 20 depicted in FIG. 1, the body 121 of the flow modulator assembly 120 is constructed and arranged for at least partial positioning in the osmotic delivery system enclosure 142. The osmotic delivery system flow modulator assembly 120 may also be made from the materials from which the osmotic delivery system flow modulator 20 assembly may be made. Likewise, the delivery path 132 of the osmotic delivery system flow modulator assembly 120 may also be configured like the delivery path 32 of the flow modulator assembly 20. Thus, it is apparent that the flow modulator 120 is similar in many aspects to the flow modulator 20. However, the flow modulator body 121 of the flow modulator assembly 120, as shown in FIGS. 5 and 6, only includes one hole 124 which communicates the opposing ends 137, 138 of the flow modulator body 121. As described below, the hole 124 may function as both a fill hole and a vent hole.

In assembling the osmotic delivery system 140, the movable dividing member 146 is first inserted into a first opening of the enclosure 142. The osmotic agent 147 is then positioned or placed through the same first opening such that is adjacent to the movable dividing member 146. Thereafter, the semipermeable plug 148 is inserted into the same first opening, effectively sealing this opening. The osmotic delivery system 140 is then preferably rotated such that the second opening of the enclosure 142 located opposite from the semipermeable plug 148 faces vertically upward.

At this point, the beneficial agent 144 may be delivered to the interior of the enclosure 144 through the hole 124 in the flow modulator body 121. Thus, when assembling the osmotic delivery system 140 according to the present invention, the flow modulator body 121 may be inserted at least partially into the second opening of the enclosure 142 opposite the semipermeable plug before the beneficial agent 144 is delivered into the system. The flow modulator body 121 is preferably inserted in the enclosure 142 such that both ends 137, 138 of the flow modulator body are within the interior of the enclosure 142.

Thereafter, a pipette, syringe, or other similar filling device, preferably filled with the same beneficial agent 144, is arranged above the hole 124 and the beneficial agent is released into the hole at a predetermined rate, delivering the beneficial agent into the interior of the enclosure 142 through the hole 124. The predetermined rate of release of beneficial agent 144 from the pipette is such that air or gas within the beneficial agent and the enclosure 142 has the opportunity to escape through the hole 124 as incoming beneficial agent is delivered through the hole 124 and fills the interior of the enclosure 142. Thus, it is apparent that the hole 124, and all of its possible configurations such as that discussed above in regard to the holes 22, 24 acts as means for venting the osmotic delivery system 140 when the beneficial agent 144 is inserted into the osmotic delivery system. Hence, the hole 124 functions as both a fill hole and a vent hole. The beneficial agent 144 is delivered for a predetermined period of time such that the beneficial agent fills the enclosure 142 and the hole 124 of the flow modulator body 121.

Alternatively, a portion of the beneficial agent 144 may be first delivered into the enclosure 142, and then the flow modulator body 121 may be at least partially inserted into the second opening of the enclosure such that the remainder of the beneficial agent may be delivered into the enclosure through the hole 124.

After the beneficial agent has been delivered into the enclosure 142, the stopper 170 illustrated in FIGS. 5-7 is inserted into the hole 124. As illustrated in FIG. 6, the stopper 170 is a pin-like member having a tip 173 and a head 175 located opposite from one another. The stopper 170 also includes a shaft 171 located between the tip 173 and the head 175. The shaft 171 is configured and sized to fit in the hole 124 of the flow modulator 120 such that a seal is formed between the exterior surface 179 of the shaft 171 and the interior surface of the hole 124. Thus, the stopper 170 functions similar to the caps 26 depicted in FIG. 3. As such, the stopper 170 may be fashioned from a material similar to that of the osmotic delivery system flow modulator 120, and should sufficiently seal the hole 124 from the environment of use such that external liquids from the environment of use do not leak into the osmotic delivery system, and such that pressures generated from the osmotic agent 147 within the osmotic delivery system 140 do not cause the beneficial agent 144 to leak out from the hole 124. Thus, the stopper 170 may press fit, thread into the hole 124, and/or be fixedly adhered within the hole with the assistance of an adhesive. However, the stopper 170 need not be a pin-shaped member. A plug, cork, peg, pin, insert, molten plastic, rod, check valve, lid, top, cap or other device or item(s) may be used to stop or close the hole 124 such that the hole is sealed. However, as described below, the stopper 170 is preferably shaped as described below such that it attaches or secures a partition 160 to the flow modulator body 121.

The stopper 170 may be made from any chemically inert and biocompatible, natural, or synthetic material which is known in the art. The stopper material is preferably a non-bioerodible material which remains in the patient after use, such as titanium. The preferred titanium for the stopper 170 is similar or equal to that from which the enclosure 142 may be made from. However, the material of the stopper 170 may alternatively be a bioerodible material which bioerodes in the environment after the osmotic delivery system has dispensed the beneficial agent 144. Generally, preferred materials for the stopper 170 are those acceptable for human implantation. Furthermore, the exterior surface 179 of the shaft 171 may be coated with a material which will help form a seal between the exterior surface 179 and the interior surface of the hole 124, such as a gold plating.

As shown in FIGS. 5 and 6, the shaft 171 of the stopper 170 is cylindrical and elongated and sized to matingly fit within the hole 124 of the flow modulator body 121. Located opposite from the tip 173 and adjacent to the head 175 is a tapered section 176 which has a smaller diameter than that of the shaft 171. After the exterior surface 179 of the shaft 171 tapers to the smaller diameter of the tapered section 176, it curvingly angles at approximately 45 from the tapered section to form the arcuate surface 177 and to define the head 175 of the stopper 170. The arcuate surface 177 of the stopper 170 ends at a diameter which is larger than that of the shaft 171 and the tapered section 176.

After the beneficial agent 144 has been inserted into the enclosure 142 through the hole 124 in the flow modulator 120, the stopper 170 is inserted into the hole 124 to seal the hole in the manner described above. However, before the stopper 170 is inserted into the hole 124, the stopper is fitted with the partition 160 illustrated in FIGS. 5 and 6.

In the embodiment illustrated in FIGS. 5-7, the partition 160 is a disc-shaped member having a predetermined thickness and smooth exterior surface 161. The partition 160 is preferably made from an elastomeric material, which may be similar or equal to that of the flow modulator body 121. Two preferred materials for the partition 160 are silicone and C-Flex, manufactured by Consolidated Polymer Technologies.

The above-described preferred materials for the partition 160 are sufficiently soft and flexible such that the tip 173 of the stopper 170 may pierce through the thickness of the partition 160 and such that the partition 160 flexes as the shaft 171 is forced through a pierced slit, cut, or rip created with the tip 173. Thus, the partition 160 illustrated in FIG. 6 preferably does not include a preformed hole for receiving the stopper 170, such that the tip 173 of the stopper 170 must be forcibly pierced through the partition 160 so that the partition 160 is slidable up the shaft 171 of the stopper.

After the partition 160 has been pierced by the tip 173, the partition 160 is slid along the shaft 171 until it reaches the tapered section 176 of the stopper 170. Because the tapered section 176 of the stopper 170 is a smaller diameter than that if the shaft 171, it is adapted to receive the partition 160 such that the partition is attached to the stopper 170 and will not easily slide down the shaft 171 toward the tip 173. However, the stopper 170 need not include the tapered section 176. Although the material for the partition 160 is sufficiently elastomeric to allow the partition to slide along the shaft 171 after it is pierced by the tip 173, it is also sufficiently rigid such that it will not easily slide beyond the head 175 which has a greater diameter than that of the shaft 171 and tapered section 176. That is, the head 175 is configured to prevent the partition 160 from being removed from the head end of the stopper 170, as shown in FIG. 7. The head 175 may also be other configurations such as the top of a "T", a retaining ring, nut, bolt, item fastened to the shaft 176, or other device which prevents the partition 160 from being removed from the head end of the shaft 171. Thus, after the partition 160 has been fitted on the shaft 171 and the stopper 170 has been inserted into the hole 124, the partition is secured to the flow modulator body 121, between the flow modulator body and the head 175 of the stopper.

Although the partition 160 depicted in FIGS. 5-7 is formed from a solid and integral piece, it need not be so configured. The partition 160 may also include an opening, slit, cut, or a hole for receiving the stopper shaft 171. Thus, with such an embodiment, the tip 173 of the stopper 170 need not be sharp or pin-like to pierce the partition 160. Likewise, the partition 160 may have an indentation located at or near the center of the partition 160 to define a predetermined location where the tip 173 of the stopper 170 should pierce the partition upon application of force to the stopper.

FIG. 7 illustrates the flow modulator assembly 120 positioned in an opening of the osmotic delivery system 140. Once the partition 160 has been positioned on the tapered section 176 of the stopper 170, and the flow modulator body 121 has been press-fit into the opening of the enclosure 142, the top 178 of the head 175 of the stopper 170 may be pressed into the hole 124 such that the stopper 170 and partition 160 attached thereto are received by the opening in the enclosure 142. The stopper 170 is preferably inserted into the hole 124 until the partition 160 abuts against a surface of the enclosure 142. In this manner, the partition 161 and the surface of the enclosure 142 define a one-way seal or check valve 141 which substantially prevents liquids external of the osmotic delivery system from the entering the interior of the enclosure 142, but which also permits the beneficial agent 144 within the enclosure 142 to exit the osmotic delivery system 140. Once the stopper 170 has been inserted into the hole 124, it is apparent that the osmotic delivery system flow modulator assembly 120 is at least partially within the interior of the enclosure 142.

As shown in FIG. 7, the partition 160 abuts against the interior surface 143 of the enclosure 142 to define the check valve 141 between the exterior surface 161 of the partition 160 and the interior surface 143. Thus, when the osmotic delivery system 140 is eventually placed into an environment of use, the osmotic agent 147 imbibes fluid through the semipermeable plug 148 and expands, creating osmotic pressure within the enclosure 142. This osmotic pressure forces the beneficial agent 144 through the delivery path 132 and eventually through the check valve 141 between the exterior surface of the partition 161 and the interior surface 143 of the enclosure 142.

As shown in FIG. 7, the stopper 170 and the partition 160 attached thereto are at least partially inserted into the enclosure 142 of the osmotic delivery system 140. In the embodiment shown in FIG. 7, the flow modulator assembly 120 is fully inserted within the enclosure 142 such that the partition 160 is also fully within the enclosure 142. Thus, as described above, the partition surface 161 abuts against the interior surface 143 of the enclosure 142 to define the check valve 141. Because the check valve 141 is formed between the exterior surface 161 of the partition 160 and the interior surface 143 of the enclosure 142, it is necessary that the partition 160 be sufficiently large such that it will abut against the interior surface 143 when the flow modulator assembly 120 is inserted into the opening of the delivery system 140.

Thus, in the embodiment of the flow modulator assembly 120 depicted in FIGS. 5-7, the partition 160 has a greater diameter than that of the flow modulator body 121 to assure that the outer surface 161 of the partition 160 will abut against the interior surface 143 of the enclosure 142 when the flow modulator 120 is inserted into the enclosure.

The diameter, thickness, and material of the partition 160 control the amount of pressure required to "open" the check valve 141 so as to allow the beneficial agent 144 to flow past or through the check valve after it has travelled through the delivery channel 132.

For example, the diameter or thickness of the partition 160 may be increased such that the amount of pressure required to "open" the check valve 141 is increased. The size of the head 175 of the stopper 170 may also be varied and/or have differently shaped surfaces so as to control the "opening" check valve pressure. Furthermore, the delivery path 132 may be located elsewhere in the flow modulator assembly 120. For instance, a portion of the delivery path 132 may also be defined by the check valve 141 of the partition 160.

FIG. 8 depicts another embodiment of an osmotic delivery system 240 which includes another embodiment of a flow modulator assembly 220. The flow modulator assembly 220 is similar to the flow modulator assembly 120, and the above description of the benefits and function of the different components of the flow modulator assembly 120 also applies to the flow modulator assembly 220. Thus, features on the flow modulator assembly 220 that are similar to features on the flow modulator assembly 120 are assigned corresponding reference numbers, increased by 100. However, the stopper 270 and the partition 260 are shaped differently than that of the stopper 170 and partition 160 depicted in FIGS. 5-7. The stopper 270 and the partition 260 have larger dimensions than the stopper 170 and partition 160 such that the amount of osmotic pressure required to "open" the check valve 241 so as to allow the beneficial agent 144 to flow past or through the check valve is increased.

More specifically, the diameter and thickness of the partition 260 is greater than that of the partition 160. Because of these increased dimensions, the exterior surface 261 of the partition 260 abuts against the exterior surface of the osmotic delivery system enclosure 242 to define the check valve 241. Contrary to the check valve 141 shown in FIG. 7, the check valve 241 illustrated in FIG. 8 is formed between the exterior surface of the enclosure 242 of the osmotic delivery system 240. Thus, in this embodiment of the present invention, the head 275 of the stopper 270 and the partition 260 are not completely within the interior of the enclosure 242, but are only partially located therein such that at least a portion of the exterior surface of the partition 260 abuts against the exterior surface of the enclosure 242. However, the partition 260 may be a greater diameter such that the head 275 may be located completely within the enclosure 242 and the exterior surface of the partition may still abut against an exterior surface of the enclosure. In an alternative embodiment, not shown, the partition 160, 260 does not form a check valve. That is, the partition 160, 260 need not abut against a surface of the enclosure 142, 242, but may assist in sealing the hole 124, 224.

In reference to either of the osmotic delivery systems 140, 240, after the hole 124, 224 has been filled to a predetermined level with the beneficial agent 144, 244, the stopper 170, 270 with the partition 160,260 attached thereto in the manner described above, is inserted into the hole 124, 224 capping or sealing the hole 124, 224 such that the beneficial agent 144, 244 located within the delivery system 140, 240 will not escape from the enclosure 142, 242 save from the delivery orifice formed in the flow modulator body 121, 221.

The hole 124, 224 may be sized to accommodate the predetermined rate that beneficial agent 144, 244 is delivered into the hole and to accommodate any gas exiting the enclosure 142, 242 through the hole. Alternatively, the beneficial agent may be delivered into the enclosure with a fill tube that is received by the hole, requiring that the hole 124, 224 be larger than the diameter of the fill tube to accommodate the escaping gas. If the delivery rate of the beneficial agent 144, 244 is relatively slow, the hole 124, 224 may have a smaller diameter and/or a longer length. If the predetermined rate of delivery of beneficial agent 144, 244 into the hole 124, 224 is relatively fast, the hole 124, 224 must have a larger diameter and/or a shorter length such that the beneficial agent 144, 244 does not overflow the hole 124, 224 as it is delivered through the hole. The level that the beneficial agent 144, 244 reaches within the hole 124, 224 at the end of the filling process may be selected such that when the stopper 170, 270 is inserted into the hole, little or no beneficial agent is expelled from the top of the hole 124, 224 due to the stopper 170, 270 occupying a portion of the space of the fill hole 124, 224.

Alternatively, the beneficial agent 144, 244 may be forced into and through the hole 124, 224 such that gas or air is forced out of the enclosure 142, 242 through the delivery path 132, 232.

Because the flow modulator assembly 120, 220 forms a seal, except for the delivery path 132, 232, with the interior surface 143, 243 of the enclosure 142, 242 the hole 124, 224 should be sufficiently large to accommodate the rate of escaping air or gas from within the enclosure 142, 242, which roughly equals the rate that the beneficial agent 144, 244 is delivered into the fill hole 124, 224.

Assembling the osmotic delivery system 142, 242 in the above-described manner is advantageous because the amount of beneficial agent 144, 244 which may be wasted is reduced. When the stopper 170, 270 is positioned within the flow modulator body 121, 221, only a minute amount of surplus beneficial agent 144, 244 is expelled from the enclosure of the osmotic delivery system 140, 240. This reduced amount of beneficial agent 144, 244 expelled when assembling an osmotic delivery system 140, 240, as compared to past assembly methods, reduces the cost of assembly. Because the amount of wasted beneficial agent is reduced, it is also easier to determine the precise amount of beneficial agent 144, 244 remaining in the osmotic delivery system 140, 240 for eventual delivery.

As described above, when delivering the beneficial agent 144, 244 into the osmotic delivery system 140, 240, the hole 124, 224 permits gas within the enclosure of the osmotic delivery system to escape from the system. Thus, when the osmotic delivery system 140, 240 is completely assembled, the amount of gas within the system is reduced. This reduction of trapped air or gas within the system is advantageous because the time to start-up of delivery of beneficial agent 144, 244 from the delivery system to the environment of use is reduced.

When the osmotic delivery system 140, 240 is eventually placed into an environment of use, the osmotic agent 147, 247 imbibes fluid through the semipermeable plug 148, 248 and expands, creating osmotic pressure within the enclosure 142, 242. This osmotic pressure forces the beneficial agent 144, 244 through the delivery path 132, 232. Because the amount of gas or air within the enclosure 142 is reduced during assembly of the osmotic delivery system, the osmotic agent 147, 247 need not first compress air within the beneficial agent before forcing the beneficial agent into the delivery path 132, 232. Hence, the start-up period to delivery of the beneficial agent 144, 244 is not delayed by the amount of time which would ordinarily be necessary to compress air pockets within the osmotic delivery system 140, 240. Furthermore, the chance that significant amounts of air or gas may expel from the system, causing possible health risks, is reduced.

The check valve 141, 241 defined by the partition 160, 260 and a surface of the enclosure 142, 242 is advantageous because it reduces the possibility of the inward flux of materials from the environment of use into the osmotic delivery system 140, 240. That is, the check valve 141, 241 reduces the chances of contaminants from entering the interior of the enclosure 142, 242, possibly destabilizing, diluting, or altering the beneficial agent formulation 144, 244. The check valve 141, 241 permits the desired rate of beneficial agent 144, 244 to exit from the osmotic delivery system 140, 240, while also controlling the diffusion of liquids from the environment of use into the system. This is further advantageous because the delivery path 132, 232 may be made larger such that it can accommodate difficult-to-deliver viscous or multi-phased beneficial agent formulations without a substantial risk of back diffusion of substances into the osmotic delivery system 140, 240. Thus, the delivery path 132, 232 need not be sized such that the average linear velocity of the beneficial agent 144, 244 through the path is higher than that of the linear inward flux of materials in the environment of use due to back diffusion because the check valve 141, 241 substantially prevents liquids external of the osmotic delivery system from entering the osmotic delivery system.

A further advantage of the osmotic delivery system 140, 240 having the flow modulator assembly 120, 220 is that the system does not need to be capped to prevent evaporation of the beneficial agent 144 from the delivery path 132, 232 of the system because the partition 160 acts as a cap or seal to prevent such evaporation. Accordingly, the osmotic delivery system 140, 240 is simpler to manufacture than conventional osmotic delivery systems while substantially preventing evaporation of the beneficial agent 144 from the system.

Figure 9:
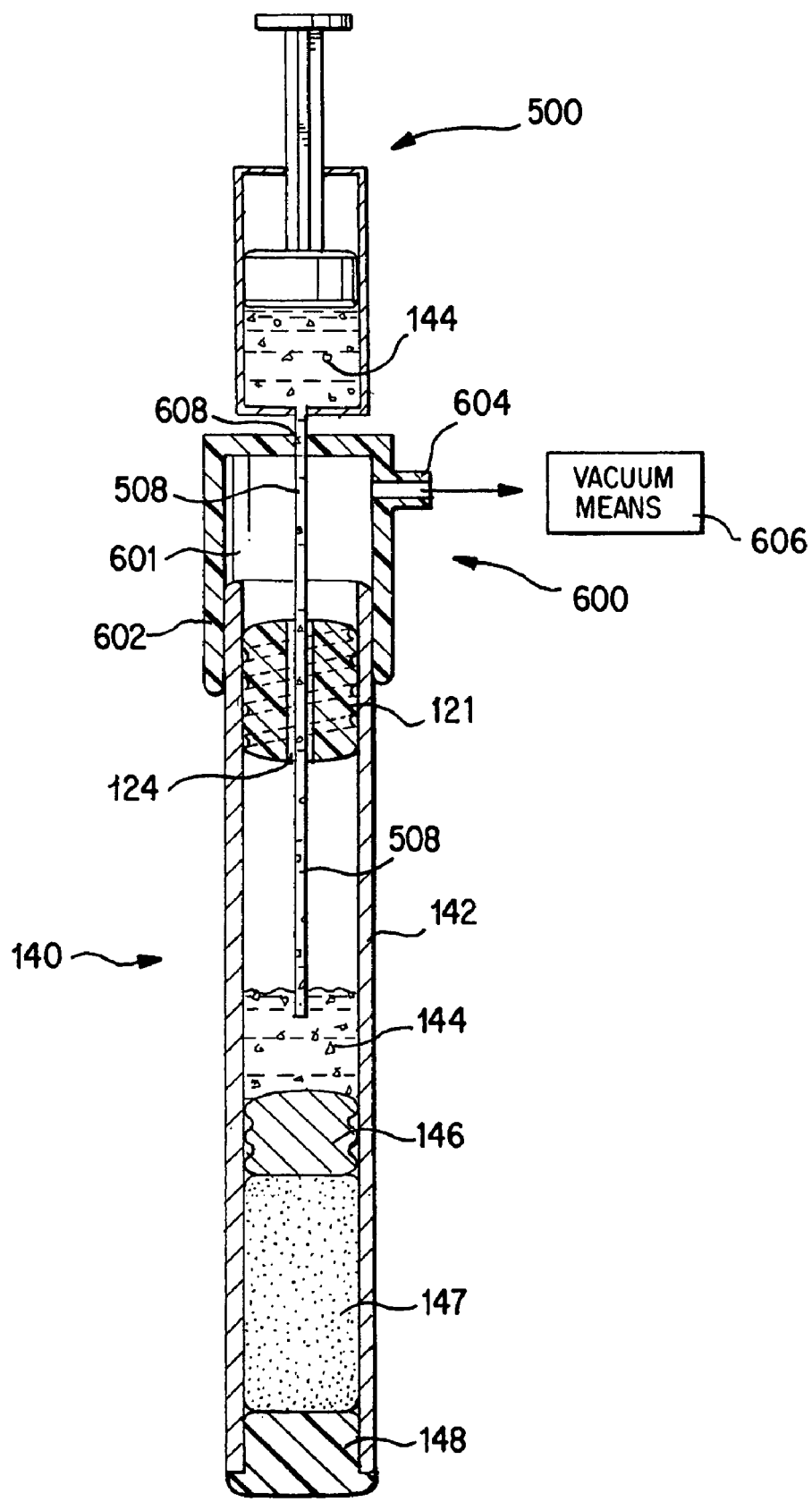
FIG. 9 is a cross-sectional side view of the assembly of an osmotic delivery system according to one embodiment of the present invention.

FIG. 9 illustrates that the hole 124 of the flow modulator body 121 may also be used in conjunction with a vacuum creating means 605, such as a vacuum pump to further remove gas from the osmotic delivery system. As shown in FIG. 9, the vacuum fixture 600 includes a first opening 608 for receiving a delivery tube 508 of a beneficial agent delivery device 500. The vacuum fixture 600 also includes a second opening 604 for connecting the interior of the vacuum fixture to the vacuum creating means 600.

The vacuum fixture 600 includes a third opening formed by the wall 602 of the vacuum fixture which is sized and shaped to form a seal with the exterior surface of the enclosure 142 when the enclosure is received by the third opening.

After the flow modulator body 121 has been inserted into the enclosure 142, the third opening of the vacuum fixture 600 may be snugly pressed over the second opening of the enclosure 142 such that at least a portion of the enclosure is within the vacuum fixture 600. Thereafter, the delivery tube 508 is inserted into the first opening 608 and the vacuum means 606 is connected to the second opening 604. Preferably, the vacuum means 606 is initiated before any beneficial agent 144 is delivered or inserted into the enclosure 142. The initiated vacuum means 606 creates a vacuum adjacent to the flow modulator body 121, defining the vacuum area 601 within vacuum fixture 600. For example, a vacuum of approximately 27 inches of mercury may be created by the vacuum means 606. Hence, it is preferable that the first opening 608 form a seal with the delivery tube 508 and that the wall 602 form a seal with the exterior surface of the enclosure 142.

Because a vacuum exists within the vacuum area 601, adjacent the flow modulator body 121, the interior of the osmotic delivery system enclosure 142 is also vented or evacuated via the hole 124 in the flow modulator body 121 such that the amount of gas within the osmotic delivery system is substantially reduced. After the gas has been removed from the osmotic delivery system 140 in the above-described manner, the beneficial agent 144 is preferably delivered into the enclosure 142 through the hole 124 in the flow modulator body 121 via the delivery tube 508 of the beneficial agent delivery device 500. Once the beneficial agent 144 has been delivered into the enclosure 142 and has at least partially filled the hole 124, the vacuum means may be shut-off and the vacuum fixture 600 removed from the enclosure. Thereafter, the assembly of the osmotic delivery system 140 may be completed by inserting the stopper 170 into the hole 124.

By creating a vacuum adjacent to the flow modulator body 121 before delivery of the beneficial agent 144 into the enclosure 142 and/or while inserting the beneficial agent 144 through the hole 124, the amount of gas within the osmotic delivery system is reduced. In addition, even if a small amount of gas bubbles were somehow trapped within the enclosure 142 of the osmotic delivery system 140, such gas bubbles will collapse after the vacuum has been removed and the system is exposed to atmospheric pressure such that the collapsed bubbles dissolve into the beneficial agent formulation 144. Hence, after the assembly of the delivery system 140 is completed and the system is eventually placed into an environment of use, the start-up period to delivery of the beneficial agent 144 is not delayed by the amount of time ordinarily required to compress gas pockets within the osmotic delivery system 140.

The above-described process may also be advantageously performed during the assembly of the osmotic delivery system 40 illustrated in FIG. 4. It will also be realized that other methods and apparatus may be used to create a vacuum adjacent to the flow modulator body 121 within the knowledge of those skilled in the art. For example, the vacuum may be created by directly applying vacuum creating means to the hole 124 of the flow modulator body 121, rather than the enclosure 142.

The above description of the preferred and alternative embodiments of the present invention must be considered as illustrative only of the principle of the invention and not limitative. Indeed, it may be easily understood that numerous modifications could be made by those skilled in the art without departing from the spirit of the invention as defined in the claims below.

What is claimed is:

1. An osmotic delivery system comprising:
  an enclosure having an opening and an interior for holding a liquid swellable osmotic agent and a beneficial agent, the enclosure provided with a semipermeable portion, the liquid swellable osmotic agent for imbibing liquid from a surrounding environment through the semipermeable portion and causing a delivery rate of the beneficial agent from the enclosure;
  an osmotic delivery system flow moderator assembly having a flow moderator body at least partially positioned in the opening of the enclosure, the body having two opposing ends and means for venting the osmotic delivery system when the beneficial agent is inserted into the osmotic delivery system, wherein the venting means is a vent hole located through the body, the vent hole communicating the opposing ends;
  a delivery path located separate from the venting means for delivering the beneficial agent from the osmotic delivery system, the delivery path being formed in at least one of the enclosure and the flow moderator assembly;

a stopper at least partially positioned in the vent hole to seal the vent hole the stopper including a shaft, a head, and tip located opposite from the head; and a partition secured to the flow moderator body, the partition being secured between the flow moderator body and the head of the stopper.

2. The osmotic delivery system according to claim 1, wherein the partition is an elastomeric material.

3. An osmotic delivery system comprising:

an enclosure having an opening and an interior for holding a liquid swellable osmotic agent and a beneficial agent, the enclosure provided with a semipermeable portion, the liquid swellable osmotic agent for imbibing liquid from a surrounding environment through the semipermeable portion and causing a delivery rate of the beneficial agent from the enclosure;

an osmotic delivery system flow moderator assembly having a flow moderator body at least partially positioned in the opening of the enclosure, the body having two opposing ends and means for venting the osmotic delivery system when the beneficial agent is inserted into the osmotic delivery system;

a delivery path located separate from the venting means for delivering the beneficial agent from the osmotic delivery system, wherein an exterior surface portion of the flow modulator body contacts and cooperates with an interior surface of the enclosure to define the delivery path; and a check valve located between the surrounding environment and the interior of the enclosure, the check valve including a surface of a partition which abuts against a surface of the enclosure.

4. The osmotic delivery system according to claim 3, wherein the surface of the enclosure is an interior surface of the enclosure.

5. The osmotic delivery system according to claim 3, wherein the surface of the enclosure is an exterior surface of the enclosure.

6. An osmotic delivery system comprising:

an enclosure having an opening and an interior for holding a liquid swellable osmotic agent and a beneficial agent, the enclosure provided with a semipermeable portion, the liquid swellable osmotic agent for imbibing liquid from a surrounding environment through the semipermeable portion and causing a delivery rate of the beneficial agent from the enclosure;

an osmotic delivery system flow moderator assembly having a flow moderator body at least partially positioned in the opening of the enclosure, the body having two opposing ends, and means for venting the osmotic delivery system when the beneficial agent is inserted into the osmotic delivery system, wherein the venting means is a vent hole located through the body, the vent hole communicating the opposing ends;

a delivery path located separate from the venting means for delivering the beneficial agent from the osmotic delivery system, wherein an exterior surface portion of the flow modulator body contacts and cooperates with an interior surface of the enclosure to define the delivery path; and a check valve formed between a surface of a partition and a surface of the enclosure for substantially preventing a liquid external of the osmotic delivery system from entering the interior of the osmotic delivery system, the check valve allowing the beneficial agent to exit the osmotic delivery system to the surrounding environment.

7. The osmotic delivery system according to claim 6, wherein the surface is an interior surface of the enclosure of the osmotic delivery system.

8. The osmotic delivery system according to claim 6, wherein the partition is secured to the flow moderator body with a stopper positioned in the hole of the flow moderator, the stopper sealing the hole located through the body.

* * * * *